(12) United States Patent
Hong et al.

(10) Patent No.: US 12,275,004 B2
(45) Date of Patent: Apr. 15, 2025

(54) CATALYST FOR SYNTHESIZING DIMETHYLETHER OR METHYLACETATE FROM SYNTHETIC GAS, METHOD FOR PREPARING THE SAME, AND METHOD FOR PREPARING DIMETHYLETHER OR METHYLACETATE USING THE SAME

(71) Applicants: HYUNDAI MOTOR COMPANY, Seoul (KR); KIA CORPORATION, Seoul (KR); RESEARCH & BUSINESS FOUNDATION SUNGKYUNKWAN UNIVERSITY, Suwon-si (KR)

(72) Inventors: Chae Hwan Hong, Seoul (KR); Jin Woo Choung, Suwon-si (KR); Young Gul Hur, Uiwang-si (KR); Jong Wook Bae, Suwon-si (KR); Hyun Seung Jung, Suwon-si (KR)

(73) Assignees: HYUNDAI MOTOR COMPANY, Seoul (KR); KIA CORPORATION, Seoul (KR); RESEARCH &BUSINESS FOUNDATION SUNGKYUNKWAN UNIVERSITY, Suwon (KR)

( * ) Notice: Subject to any disclaimer, the term of this patent is extended or adjusted under 35 U.S.C. 154(b) by 0 days.

(21) Appl. No.: 18/233,457

(22) Filed: Aug. 14, 2023

(65) Prior Publication Data

US 2023/0382843 A1    Nov. 30, 2023

Related U.S. Application Data

(62) Division of application No. 17/470,122, filed on Sep. 9, 2021, now Pat. No. 11,767,285.

(30) Foreign Application Priority Data

Apr. 29, 2021 (KR) .......................... 10-2021-0055654

(51) Int. Cl.
*B01J 29/72* (2006.01)
*B01J 21/04* (2006.01)
(Continued)

(52) U.S. Cl.
CPC ............... *B01J 29/72* (2013.01); *B01J 21/04* (2013.01); *B01J 23/06* (2013.01); *B01J 29/65* (2013.01);
(Continued)

(58) Field of Classification Search
CPC ... B01J 29/72; B01J 29/68; B01J 29/65; B01J 21/04; B01J 23/06; B01J 35/395; B01J 29/80
See application file for complete search history.

(56) References Cited

FOREIGN PATENT DOCUMENTS

KR    2009-0011459 A    2/2009
KR    20090011459    *    2/2009    ............. B01J 21/04

OTHER PUBLICATIONS

Xu, H et al., Preparation of Aluminosilicate Ferrierite Zeolite Nanosheets with controllable thickness n the presence of a sole organic structure directing agent, Molecules, 25, 771, pp. 1-10 (Year: 2020).*
(Continued)

*Primary Examiner* — Yate' K Cutliff
(74) *Attorney, Agent, or Firm* — MCDONNELL BOEHNEN HULBERT & BERGHOFF LLP

(57) ABSTRACT

The present disclosure provides a method of preparing a catalyst for synthesizing dimethyl ether or methylacetate from synthetic gas that includes preparing a nanosheet ferrierite zeolite (FER), and co-precipitating the nanosheet ferrierite zeolite and a precursor of a Cu—Zn—Al-based oxide (CZA) to obtain a hybrid CZA/FER catalyst.

3 Claims, 10 Drawing Sheets

(51) Int. Cl.
  *B01J 23/06* (2006.01)
  *B01J 29/65* (2006.01)
  *B01J 29/68* (2006.01)
  *B01J 29/80* (2006.01)
  *B01J 35/30* (2024.01)
  *B01J 37/03* (2006.01)
  *B01J 37/04* (2006.01)
  *B01J 37/08* (2006.01)
  *B01J 37/10* (2006.01)
  *B01J 37/30* (2006.01)
  *C07C 29/156* (2006.01)
  *C07C 41/09* (2006.01)
  *C07C 43/04* (2006.01)
  *C07C 67/37* (2006.01)

(52) U.S. Cl.
  CPC ............... *B01J 29/68* (2013.01); *B01J 29/80* (2013.01); *B01J 35/395* (2024.01); *B01J 37/035* (2013.01); *B01J 37/04* (2013.01); *B01J 37/082* (2013.01); *B01J 37/10* (2013.01); *B01J 37/30* (2013.01); *C07C 29/156* (2013.01); *C07C 41/09* (2013.01); *B01J 2229/18* (2013.01); *C07C 43/043* (2013.01); *C07C 67/37* (2013.01)

(56) References Cited

OTHER PUBLICATIONS

Sai Prasad, P.S., et al., Single-step syntehsis of DME form syngas on Cu—Zn0—Al2O3/zeolite bifunctional catalyst: The superiority of ferrierite over other zeolites, Fuel Processing Technology, 89, pp. 1281-1286 (Year: 2008).*

Faisal Zafar et al., "One step conversion of CO2 containing syngas to DME over hybridized CuZnAl with Ferrierite catalyst", The Korean Society of Industrial and Engineering Chemistry, Oct. 28, 2020, Kimdaejung Convention Center, Gwangju—Abstract Only.

KR 20090011459 (A), Won, et al., Catalyst for direct synthesis of dimethyl ether from syngas and preparation method thereof, English Translation, 17 pages (Year: 2009).

Bae, et al., Effect of precipitants during the preparation of Cu—ZnO—Al2O3/Zr-ferrierite catalyst on the DME synthesis from syngas, Journal of Industrial and Engineering Chemistry, vol. 15, issue 4, pp. 566-572 (Year: 2009).

Xu, et al., Preparation of aluminosilicate ferrierite zeolite nanosheets with controllable thickness in the presence of a sole organic structure directing agent, Molecules, 25, 771, pp. 1-10 (Year: 2020).

* cited by examiner

CATALYST FOR SYNTHESIZING DIMETHYLETHER OR METHYLACETATE FROM SYNTHETIC GAS, METHOD FOR PREPARING THE SAME, AND METHOD FOR PREPARING DIMETHYLETHER OR METHYLACETATE USING THE SAME

CROSS REFERENCE TO RELATED APPLICATIONS

The present application is a Divisional of U.S. application Ser. No. 17/470,122, filed Sep. 9, 2021, which claims priority to Korean Patent Application No. 10-2021-0055654 filed in the Korean Intellectual Property Office on Apr. 29, 2021, the entire contents of which are incorporated herein by reference.

BACKGROUND

(a) Field

The present disclosure relates to a catalyst for synthesizing dimethylether or methylacetate from synthetic gas composed of carbon monoxide (CO), carbon dioxide ($CO_2$), and hydrogen ($H_2$), a method for preparing the same, and a method for preparing dimethylether or methylacetate using the same.

(b) Description of the Related Art

As a concentration of harmful materials such as $CO_2$, CO, $CH_4$, $NO_x$, and the like in the atmosphere increases due to the rapid development of chemical industries, a method of utilizing these harmful materials is being actively researched by using various metal catalysts.

In this process, noble metals may be used due to high reactivity but are not economical. On the contrary, a CZA catalyst composed of relatively inexpensive copper, zinc, and alumina may successfully convert carbon monoxide (CO) and efficiently synthesize methanol used for various purposes in the overall chemical industries.

Furthermore, since the methanol may be converted into dimethylether (DME) in an acid catalyst, a hybrid catalyst of the CZA catalyst and the acid catalyst may be synthesized, and this reaction may be represented by Reaction Schemes 1 and 2.

$CO + 2H_2 \rightarrow CH_3OH$   Reaction Scheme 1:

$2CH_3OH \leftrightarrow CH_3OCH_3 + H_2O$   Reaction Scheme 2:

On the other hand, after the reaction of converting carbon monoxide into dimethylether, methylacetate (MA) is synthesized through a carbonylation reaction of the dimethylether, and then, ethanol may be synthesized from the methylacetate (MA) through a hydrogenation reaction. This reaction may be represented by Reaction Schemes 3 to 5.

$2CO + 4H_2 \rightarrow CH_3OCH_3 + H_2O$   Reaction Scheme 3:

$CH_3OCH_3 + CO \rightarrow CH_3COOCH_3$   Reaction Scheme 4:

$CH_3COOCH_3 + H_2 \rightarrow CH_3OH\ C_2H_5OH$   Reaction Scheme 5:

The above reactions are eco-friendly and economical because it is possible to selectively synthesize ethanol as well as methanol through the conversion of carbon monoxide. In addition, since DME and MA synthesized during the reaction are each used as fuel or intermediates of various pharmaceutical chemicals, carbon monoxide may be more effectively recycled by controlling these processes.

SUMMARY

The present disclosure provides a catalyst in which an amount of Brönsted acid sites that are active sites of the dimethyl ether (DME) conversion reaction from synthetic gas is optimized, reaction sites are introduced more evenly and stably to have excellent activity in the DME synthesis reaction, and deactivation of the catalyst is suppressed when methyl acetate (MA) is synthesized from dimethyl ether.

The present disclosure also provides a method for preparing the catalyst.

The present disclosure also provides a method for preparing dimethylether (DME) or methylacetate (MA) from synthetic gas using the catalyst.

According to an embodiment, a method of preparing a catalyst for synthesizing dimethyl ether or methylacetate from synthetic gas includes preparing a nanosheet ferrierite zeolite (FER), and co-precipitating the nanosheet ferrierite zeolite and a precursor of a Cu—Zn—Al-based oxide (CZA) to obtain a hybrid CZA/FER catalyst.

The preparing of the nanosheet ferrierite zeolite may include adding a silica source, an alumina source, an organic template material, and a structural derivative material to a basic aqueous solution to preparing a precursor mixed solution, synthesizing a zeolite by hydrothermal synthesis of the precursor mixed solution, and ion-exchanging the zeolite.

The preparing of the precursor mixed solution may include adding a silica source to the basic aqueous solution to prepare a basic silica solution, adding an organic template material and a structural derivative material to the basic silica solution to prepare a mixed solution, and adding an alumina source to the mixed solution to prepare a precursor mixed solution.

The organic template material may be a linear organic compound having 15 to 30 carbons and at least one nitrogen.

The organic template material may include cetrimonium bromide (CTAB), sodium dodecyl sulfate, ammonium lauryl sulfate, or a combination thereof.

The structural derivative material may be a nitrogen-containing heterocyclic compound including pyrrolidine, piperidine, or a combination thereof.

The organic template material and the structural derivative material may be added in a mole ratio of about 0.01:1 to about 0.5:1.

The hydrothermal synthesis of the precursor mixed solution may be performed at about 120° C. to 180° C. for about 96 hours to 168 hours.

The preparing of the nanosheet ferrierite zeolite may further include calcining the hydrothermal synthesized zeolite at about 450° C. to about 650° C. for about 3 hours to about 6 hours to prepare an Na-form zeolite.

The ion-exchanging of the zeolite may include exchanging the Na-form zeolite with a cation to prepare an $NH_3$-form zeolite.

The preparing of the nanosheet ferrierite zeolite may further include calcining the ion-exchanged zeolite at about 450° C. to about 650° C. for about 3 hours to about 6 hours to convert the ion-exchanged zeolite into a H-form zeolite.

The co-precipitating may include preparing a first solution including the nanosheet ferrierite zeolite, preparing a second solution including a copper precursor, a zinc precursor, and an aluminum precursor, preparing a third solution including a basic precipitating agent, and adding the second solution and the third solution to the first solution to perform co-precipitating.

A mole ratio of Cu:Zn:Al in the second solution may be about 10 to 5:5 to about 1:1.

The copper precursor may include an acetate, a hydroxide, a nitrate, or a combination thereof of copper, the zinc precursor may include an acetate, a hydroxide, a nitrate, or a combination thereof of zinc, and the aluminum precursor may include an acetate, a hydroxide, a nitrate, or a combination thereof, of aluminum.

The basic precipitating agent may include sodium carbonate, potassium carbonate, ammonium carbonate, sodium bicarbonate, or a combination thereof.

In the co-precipitating process, the second solution and the third solution may be dropped dropwise to the first solution to co-precipitate them.

The co-precipitating may be performed at a temperature of about 65° C. to about 75° C. and a pH of less than or equal to about 7.

The co-precipitating may further include growing a crystal of the prepared precipitate for about 1 hour to about 2 hours.

The co-precipitating may further include calcining the prepared precipitate at about 200° C. to about 600° C. for about 2 hours to about 6 hours.

According to another embodiment, a hybrid CZA/FER catalyst includes a nanosheet ferrierite zeolite and a Cu—Zn—Al-based oxide supported on the nanosheet ferrierite zeolite.

The Cu—Zn—Al-based oxide may include about 40 wt % to about 60 wt % of CuO, about 35 wt % to about 45 wt % of ZnO, and about 5 wt % to about 15 wt % of $Al_2O_3$ based on the total weight of the Cu—Zn—Al-based oxide.

The hybrid CZA/FER catalyst may include about 0.1 part by weight to about 5 parts by weight of the Cu—Zn—Al-based oxide based on 1 part by weight of the nanosheet ferrierite zeolite.

A Si/Al ratio of the nanosheet ferrierite zeolite may be about 5 to about 30.

The nanosheet ferrierite zeolite may have a shape in which one or more sheets having a thickness of about 4 nm to about 70 nm and a width of about 100 nm to about 150 nm are stacked.

According to another embodiment, a method for preparing dimethyl ether includes selectively preparing dimethyl ether through a conversion reaction of synthetic gas using the hybrid CZA/FER catalyst.

In the method for preparing dimethyl ether, the synthetic gas may include hydrogen ($H_2$) and carbon monoxide (CO) in a mole ratio of about 1:2.5 to about 1:7.5, and may include about 8 mol % to about 30 mol % of carbon monoxide based on the total amount of the synthetic gas.

According to another embodiment, a method for preparing methyl acetate includes selectively preparing methyl acetate and methanol through the carbonylation of dimethyl ether using a hybrid CZA/FER catalyst.

In the method for preparing methyl acetate, a reaction gas may include dimethyl ether (DME) and carbon monoxide (CO) in a mole ratio of about 1:9 to about 1:50, and may include carbon monoxide in an amount of about 45 mol % to about 90 mol % based on the total amount of the reaction gas.

According to another embodiment, a method for preparing methyl acetate includes synthesizing methyl acetate from synthetic gas via dimethyl ether at once, using a nanosheet ferrierite zeolite and a hybrid CZA/FER catalyst.

In the method for preparing methyl acetate, the synthetic gas may include hydrogen ($H_2$) and carbon monoxide (CO) in a mole ratio of about 1:2.5 to about 1:7.5, and may include about 8 mol % to about 30 mol % of carbon monoxide based on the total amount of the synthetic gas.

The method for preparing methyl acetate may be performed using a fixed-bed reactor in which a hybrid CZA/FER catalyst is loaded on the upper layer and nanosheet ferrierite zeolite is loaded on the lower layer, and a weight ratio of the hybrid CZA/FER catalyst and the nanosheet ferrierite zeolite in the fixed-bed reactor may be about 1:1 to about 1:2.

In the catalyst, the amount of 8-membered-ring Brönsted acid sites, which is the active site of the dimethyl ether (DME) conversion reaction, is optimized, and the catalyst may more evenly and stably introduce the reaction sites for the dimethyl ether conversion reaction of synthetic gas due to its thin thickness and large specific surface area, and thus has improved activity in the DME synthesis reaction.

In addition, the catalyst deactivation is suppressed by reducing the amount of coke deposited when synthesizing methyl acetate (MA) from dimethyl ether due to smoother mass transfer on the catalyst due to its thin thickness and large specific surface area.

In addition, since the catalyst simultaneously includes a reaction site at which CO is converted to methanol and a reaction site at which methanol is converted to dimethyl ether (DME), dimethylether (DME) may be successfully synthesized from synthetic gas composed of carbon monoxide (CO), carbon dioxide ($CO_2$) and hydrogen ($H_2$), and dimethyl ether may also be easily converted to methyl acetate (MA), that is, an important chemical species.

DETAILED DESCRIPTION

Figure 1:
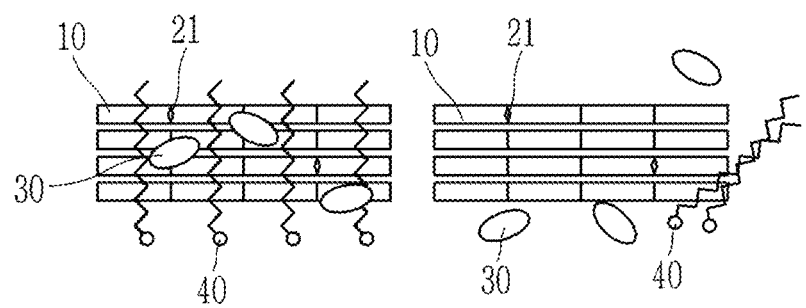
FIG. 1 is a schematic view illustrating a process for preparing a catalyst according to an embodiment.

The advantages and features of the present disclosure and the methods for accomplishing the same will be apparent from the embodiments described hereinafter with reference to the accompanying drawings. However, the embodiments should not be construed as being limited to the embodiments set forth herein. Unless otherwise defined, all terms (including technical and scientific terms) used herein have the same meaning as commonly understood by one of ordinary skill in the art. In addition, terms defined in a commonly used dictionary are not to be ideally or excessively interpreted unless explicitly defined.

In addition, unless explicitly described to the contrary, the word "comprise", and variations such as "comprises" or "comprising," will be understood to imply the inclusion of stated elements but not the exclusion of any other elements.

Further, the singular includes the plural unless mentioned otherwise.

A method of preparing a catalyst according to an embodiment includes preparing a nanosheet ferrierite zeolite (FER), and co-precipitating the nanosheet ferrierite zeolite and a precursor of a Cu—Zn—Al-based oxide (CZA) to obtain a hybrid CZA/FER catalyst. The catalyst may be used as a catalyst for synthesizing dimethylether or methylacetate from synthetic gas.

For example, the preparing of the nanosheet ferrierite zeolite may include adding a silica source, an alumina source, an organic template material, and a structural derivative material to a basic aqueous solution to preparing a precursor mixed solution, synthesizing a zeolite by hydrothermal synthesis of the precursor mixed solution, and ion-exchanging the zeolite. In other words, the nanosheet ferrierite zeolite is synthesized using a structural derivative material that plays a key role in the formation of a unique framework structure of ferrierite and an organic template material that imparts special properties.

For example, the preparing of the precursor mixed solution may include adding a silica source to the basic aqueous solution to prepare a basic silica solution, adding an organic template material and a structural derivative material to the basic silica solution to prepare a mixed solution, and adding an alumina source to the mixed solution to prepare a precursor mixed solution.

The basic aqueous solution may be an aqueous alkali hydroxide solution including sodium hydroxide, potassium hydroxide, calcium hydroxide, magnesium hydroxide, or a combination thereof.

The silica source may include a silica sol, a silica gel, a silica hydrogel, a silica hydroxide, a fumed silica, a precipitated silica, a sodium silicate, a tetraalkylorthosilicate, or combinations thereof.

The aluminum source may include sodium aluminate ($NaAlO_2$), $AlCl_3$, $Al_2(SO_4)_3$, aluminum hydroxide ($Al(OH)_3$), kaolin, clay, or a combination thereof.

The silica source and the aluminum source may be added in a mole ratio of about 5:1 to about 30:1, for example, about 10:1. When the mole ratio of the silica/aluminum source is less than about 5, the amount of acid sites serving as the reaction site may be too small, and the reactivity may be severely reduced. When the mole ratio of the silica/aluminum source is greater than about 30, aluminum is excessively embedded in the ferrierite structure, the strength of the acid spots may be weakened or the ferrierite characteristic crystal itself may not be formed.

The organic template material may be a linear organic compound containing 15 to 30 carbons and at least one nitrogen.

For example, the organic template material may include 10 to 30 carbons, 10 or more carbons form a chain bond, and may be a material including an ionic moiety. For example, the organic template material may include cetrimonium bromide (CTAB), sodium docecyl sulfate, ammonium lauryl sulfate, or a combination thereof.

The structural derivative material may be a nitrogen-containing heterocyclic compound including pyrrolidine, piperidine, or a combination thereof.

The structural derivative may be added in an amount of about 0.2 to about 2.0 parts by mole, for example, about 0.8 parts by mole to about 1.0 part by mole based on 1 part by mole of the silica source. When the amount of the structural derivative is less than about 0.2 parts by mole, the ferrierite structure itself may not be formed, and when it exceeds about 2.0 parts by mole, the amount of acid sites generated after synthesis may decrease and thus catalyst reactivity may also decrease.

Figure 2:
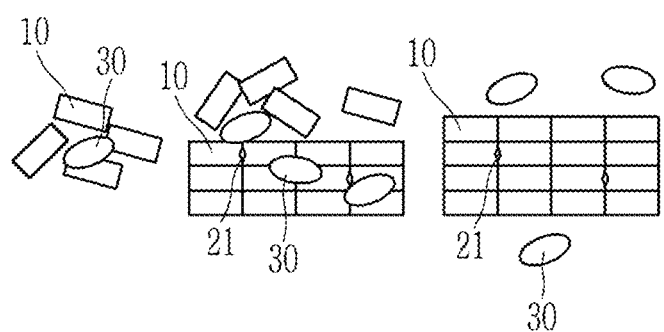
FIG. 2 is a schematic view illustrating a process for preparing a catalyst according to the prior art.

FIG. 1 is a schematic view illustrating a process for preparing a catalyst according to an embodiment and FIG. 2 is a schematic view illustrating a process for preparing a catalyst according to the prior art. Referring to FIGS. 1 and 2, when the aluminum source (not shown) and the structural derivative material 30 are added to the basic aqueous solution, the silica source 10 and the aluminum atoms 21 derived from the aluminum source are combined via the structural derivative material 30 to form a zeolite of a ferrierite structure. At this time, when the organic template material 40 having a long carbon chain is further added, the growth of the ferrierite structure is inhibited and ferrierite of a thin nanosheet structure is formed.

The organic template material and the structural derivative material may be added in a mole ratio of about 0.01:1 to about 0.5:1. If the amount of the organic template material is too large, the crystal structure of ferrierite itself is damaged, and synthesis may be difficult.

The hydrothermal synthesis of the precursor mixed solution may be performed at about 120° C. to about 180° C. for about 96 hours to about 168 hours. If the hydrothermal synthesis temperature is less than about 120° C., the crystallinity of the synthesized ferrierite may decrease, and if it exceeds about 180° C., the particle size of the synthesized catalyst may increase and the nanosheet structure may not be formed. If the hydrothermal synthesis time is less than about 96 hours, the crystallinity of the synthesized ferrierite may decrease, and if it exceeds about 168 hours, the crystal size of the synthesized ferrierite may become too large and the nanosheet structure may not be formed.

In this case, the synthesized zeolite may be a Na-form zeolite, and an $NH_3$-form zeolite may be prepared by exchanging the Na-form zeolite with a cation through the ion-exchange.

As an example, the ion-exchange may involve repeating 3 to 6 times the processes of dipping Na-form zeolite in an aqueous solution of ammonium nitrate ($NH_4NO_3$), and stirring the resultant at about 60° C. to about 80° C. for 3 hours or more to be exchanged into a $NH_4^+$ ion form and thus to prepare $NH_3$-form zeolite.

Additionally, the method may further include removing impurities, structural derivative residues, and organic template residues included in the synthesized zeolite through washing the ion-exchanged zeolite with distilled water, drying at a high temperature, or calcining at a high temperature.

For example, high-temperature calcination may convert the ion-exchanged zeolite into H-form zeolite by calcining the ion-exchanged zeolite at about 450° C. to about 650° C. for about 3 hours to about 6 hours. If the calcination reaction temperature is less than 450° C., the removal of ammonium ions may not be sufficient, so OH bonds (Brönsted acid sites) may not be sufficiently generated and if it exceeds about 650° C., the ferrierite structure itself may collapse. If the time is less than about 3 hours, the removal of ammonium ions may not be sufficient, so that the OH bond (Brönsted acid site) may not be sufficiently generated, and if it exceeds about 6 hours, the ferrierite structure itself may collapse.

The prepared nanosheet ferrierite zeolite includes 8 membered-rings. The 8 membered-rings refer to a ring-shaped structure formed by eight Al, O, and Si atoms included in zeolite, and some of about 250 zeolite-based materials include the 8 membered-rings. The conversion reaction of dimethylether into methylacetate occurs only in zeolites containing the 8 membered-rings. In other words, since ZSM-5 has no 8 membered-rings, the conversion reaction of dimethylether is impossible therein. In addition, not all the zeolites including the 8 membered-rings show activity in the dimethylether conversion reaction, but mordenite (MOR), chabazite (CHA), SUZ-4, and the like show activity. However, these zeolites are fast deactivated (particularly, MOR) or have not yet been sufficiently researched (particularly, CHA, SUZ-4).

On the contrary, since the nanosheet ferrierite zeolites may optimize an amount of the 8 membered-rings acid sites, which are active sites of the dimethylether conversion reaction, and also, have a form of stacking thin sheet structures in several layers and thus a large specific surface area and include lots of the acid sites per unit weight, and in addition, a large portion of a catalyst is exposed to outside, the dimethylether conversion reaction may stably occur, and the catalyst has the thin nanosheet structure and thus may suppress the coke deposition causing the deactivation during the reaction.

The co-precipitating may include preparing a first solution including the nanosheet ferrierite zeolite, preparing a second solution including a copper precursor, a zinc precursor, and an aluminum precursor, preparing a third solution including a basic precipitating agent, and adding the second solution and the third solution to the first solution to co-precipitate them.

For example, after dispersing the prepared nanosheet ferrierite zeolite in an aqueous solution, the mixed solution of the metal precursor including the copper precursor, the zinc precursor, and the aluminum precursor and the basic aqueous solution are simultaneously dropped and stirred in the aqueous zeolite solution, followed by stirring the resultant to prepare a hybrid CZA/FER catalyst.

The first solution may be a suspended aqueous solution prepared by mixing the prepared nanosheet ferrierite zeolite with an aqueous solution.

The metal precursor of the copper precursor, the zinc precursor, and the aluminum precursor in the second solution may include an acetate, a hydroxide, a nitrate, or a combination thereof, as a precursor of each metal. For example, the copper precursor may include an acetate, a hydroxide, a nitrate, or a combination thereof of copper, the zinc precursor may include an acetate, a hydroxide, a nitrate, or a combination thereof of zinc, and the aluminum precursor may include an acetate, a hydroxide, a nitrate, or a combination thereof of aluminum.

The mole ratio of Cu:Zn:Al in the second solution may be from about 10 to 5:5 to about 1:1, for example, from about 8 to 6:4 to about 2:1, or about 7:3:1. If the mole ratio of copper (Cu) is less than about 5, the reactivity may decrease due to insufficient formation of the reaction point Cu and if the mole ratio of copper (Cu) exceeds about 10, the reactivity may decrease or deactivation may be rapid due to severe aggregation of Cu. If the mole ratio of zinc (Zn) is less than about 1, hydrophobicity of the catalyst is weak, side reactions may proceed by water generated during the reaction, and the reactivity may be reduced, and if it exceeds about 5, the stability of Cu, the reaction point, may be weakened, and the mole ratio of aluminum (Al). If the mole ratio of aluminum (Al) is too small, the selectivity of the final product, dimethyl ether, may decrease, and if it is too large, the stability of Cu, the reaction point, may be weakened.

In the third solution, the basic precipitating agent may include sodium carbonate, potassium carbonate, ammonium carbonate, sodium bicarbonate, or a combination thereof.

When the first solution to the third solution is prepared, the second solution and the third solution may be added dropwise to the first solution to be co-precipitated. The co-precipitating may be performed at a temperature of about 65° C. to about 75° C. and a pH of less than or equal to about 7. By introducing the third solution including the basic precipitating agent, the pH of the solution in which the precursor solutions are dissolved may be adjusted.

After the second solution including the metal precursor is all consumed, the process of growing the crystal for about 1 to about 2 hours may be further included. In addition, the method may further include a process of optionally washing, drying, and calcining the hybrid CZA/FER catalyst after co-precipitating.

The drying may be performed by heating the precipitate at a temperature of about 100° C. or higher, for example, about 100° C. to about 150° C. for one or more days, and the calcining may be performed by heat treatment at about 200° C. to about 600° C. for about 2 hours to about 6 hours. If the calcining temperature is less than about 200° C., a portion of the metal precursor remains on the surface and the production of by-products may increase. When the temperature exceeds about 600° C., the surface acidity of the solid acid catalyst is changed according to the change in the oxidation state of the metal oxide, so that the production of by-products such as $CO_2$ may increase.

A hybrid CZA/FER catalyst according to another embodiment includes a nanosheet ferrierite zeolite and a Cu—Zn—Al-based oxide supported on the nanosheet ferrierite zeolite.

The hybrid CZA/FER catalyst disperses a large amount of Cu more widely compared to commercial FER due to the large specific surface area of the nanosheet ferrierite zeolite, so that Cu, the reaction point in the dimethyl ether conversion reaction of synthetic gas, is introduced more evenly and stably. That is, the hybrid CZA/FER catalyst has a high dispersion degree of Cu, is easy to reduce, and has a larger specific surface area of Cu metal, so it is possible to improve the DME production process through the conversion reaction of CO.

The Cu—Zn—Al-based oxide may include about 40 wt % to about 60 wt % of CuO, about 35 wt % to about 45 wt % of ZnO, and about 5 wt % to about 15 wt % of $Al_2O_3$ based on the total weight of the Cu—Zn—Al-based oxide. If the amount of CuO is less than about 40 wt %, a yield reduction phenomenon occurs due to a decrease in the active site for methanol synthesis, and when it exceeds about 60 wt %, it is difficult to form an appropriate catalyst structure with other metals, so that the reactivity may be reduced. If the amount of ZnO is less than 35 wt %, an appropriate porous material with CuO and $Al_2O_3$ may be prevented from being formed, and if it exceeds about 45 wt %, the reaction rate of methanol synthesis due to reduction of CuO, an active ingredient, may be reduced. If the amount of $Al_2O_3$ is less than about 5 wt %, it may be difficult to form a structure favorable to the activity of the Cu—Zn—Al-based oxide, and if it exceeds about 15 wt %, the reactivity may be reduced due to reduction of the active site for methanol synthesis.

The hybrid CZA/FER catalyst may include about 0.1 part by weight to about 5 parts by weight, for example, about 0.5 parts by weight to about 4 parts by weight of the Cu—Zn—Al-based oxide based on 1 part by weight of the mesoporous ferrierite zeolite. If the amount of the Cu—Zn—Al-based oxide is less than about 0.1 parts by weight, the activity for the methanol synthesis reaction may decrease and the yield of the entire process may decrease due to an increase in the conversion rate to $CO_2$, and if it exceeds about 5 parts by weight, the conversion rate to dimethyl ether may decrease due to the decrease of the active site of the solid acid catalyst.

A Si/Al mole ratio of the nanosheet ferrierite zeolite may be about 5 to about 30. If the Si/Al mole ratio of the nanosheet ferrierite zeolite is less than about 5, the amount of acid sites serving as a reaction point may be too small to severely decrease reactivity, and if it exceeds about 30, aluminum may be excessively embedded in the ferrierite structure, and on the contrary, the strength of the acid sites may be weakened or the ferrierite characteristic crystal itself may not be formed.

The nanosheet ferrierite zeolite may have a shape in which one or more sheets having a thickness of about 4 nm to about 70 nm and a width of about 100 nm to about 150 nm may be stacked, and for example, a sheet having a thickness of about 5 nm to about 10 nm, and a width of about 100 nm to about 120 nm may be stacked in countless layers.

The catalyst may be a hybrid CZA/FER catalyst synthesized by co-precipitating a CZA-based material composed of copper (Cu), zinc (Zn), and alumina ($Al_2O_3$) and nanosheet ferrierite zeolite (FER), and dimethyl ether (DME) may be successfully synthesized from synthetic gas composed of carbon monoxide (CO), carbon dioxide ($CO_2$) and hydrogen ($H_2$).

In addition, since the ferrierite itself used as a support may convert dimethyl ether to methyl acetate, the catalyst may successfully convert dimethyl ether and methyl acetate from synthetic gas.

At this time, the reacting CO and $CO_2$ are representative environmental pollutants, which are generated after chemical reaction in many industrial sites such as steel mills and factories and are harmful gases that are discharged into the atmosphere. Therefore, if the inevitably generated harmful gas is captured and made into synthetic gas, and then dimethyl ether and methyl acetate is synthesized using the same as a fuel, thereby solving environmental problems and creating enormous economic benefits.

The hybrid CZA/FER catalyst has Cu and the Brönsted acid site of ferrierite as reaction sites, CO reacts with $H_2$ on Cu to be converted into methanol, and methanol is converted to DME at the Brönsted acid site of ferrierite.

After synthesizing a nanosheet FER with extremely thin properties, the hybrid CZA/FER catalyst is synthesized by co-precipitating Cu, Zn, and $Al_2O_3$ into the FER.

The Cu may serve as a reaction site at which CO is converted into methanol, and the FER may serve as a support where Cu may stably exist, as well as a reaction site at which methanol may be converted into DME by providing an acid site.

In addition, the nanosheet FER is a nanosheet structure having an extremely thin structure, and is characterized by a much thinner thickness and a large specific surface area than a general FER. In addition, the amount of Brönsted acid sites, which are reaction sites, may be optimized, and mass transfer occurs smoothly on the catalyst due to its thin thickness and large area. Due to this, when synthesizing MA in DME, the amount of coke deposited may be reduced, and coke deposition may be suppressed due to the smooth removal of the coke precursor, and ultimately the deactivation of the catalyst may be suppressed. In addition, due to the large specific surface area, when Cu is co-precipitated into the nanosheet FER, a dispersion degree of Cu may increase and improved activity in the DME synthesis reaction may be exhibited.

Accordingly, the method for preparing dimethyl ether according to another embodiment can selectively prepare dimethyl ether through the conversion reaction of synthetic gas using the hybrid CZA/FER catalyst.

In the method for preparing dimethyl ether, the synthetic gas may include hydrogen ($H_2$) and carbon monoxide (CO) in a mole ratio of about 1:2.5 to about 1:7.5, and may include about 8 mol % to about 30 mol % of carbon monoxide based on the total amount of the synthetic gas. When the synthetic gas includes carbon monoxide in a mole ratio of less than about 2.5, the final dimethyl ether productivity may decrease, and when the mole ratio is greater than about 7.5, the carbon monoxide conversion rate may be lowered. In addition, when the synthetic gas includes less than 8 mol % of carbon monoxide, the final dimethyl ether productivity may decrease, and when it contains more than 30 mol %, the carbon monoxide conversion rate may be lowered.

The method for preparing methyl acetate according to another embodiment may selectively prepare methyl acetate and methanol through the carbonylation reaction of dimethyl ether using a hybrid CZA/FER catalyst.

In the method for preparing methyl acetate, the reaction gas may include dimethyl ether (DME) and carbon monoxide (CO) in a mole ratio of about 1:9 to about 1:50, and may include carbon monoxide in an amount of about 45 mol % to about 90 mol % based on the total amount of the reaction gas. If the synthetic gas includes carbon monoxide in a mole ratio of less than 9, the dimethyl ether conversion may decrease, and when the mole ratio is greater than about 50, catalyst deactivation may be accelerated. In addition, when the synthetic gas includes less than about 45 mol % of the carbon monoxide, the dimethyl ether conversion may decrease, and when it includes more than about 90 mol % of the carbon monoxide, catalyst deactivation may be accelerated.

A method for preparing methyl acetate according to another embodiment may include synthesizing methyl acetate from synthetic gas via dimethyl ether at once, using the nanosheet ferrierite zeolite and hybrid CZA/FER catalyst.

For example, dimethyl ether may be converted to methyl acetate using nanosheet ferrierite and the synthetic gas may be converted to dimethyl ether using CZA/FER. By simultaneously loading these two catalysts into one reactor in a dual-bed manner, methyl acetate may be synthesized from synthetic gas via dimethyl ether in one-step. That is, the hybrid CZA/FER catalyst may be loaded in the upper layer of the fixed-bed reactor, and the nanosheet ferrierite zeolite may be loaded in the lower layer of the fixed-bed reactor. In this case, a weight ratio of the hybrid CZA/FER catalyst to the nanosheet ferrierite zeolite may be about 1:1 to about 1:2. If the weight ratio of the ferrierite zeolite is less than about 1, the methyl acetate productivity may decrease, and if it exceeds 2, the deactivation may be accelerated in the entire catalytic reaction system.

As an example, the hybrid CZA/FER catalyst may be reduced in a hydrogen atmosphere in a range of about 200°

C. to about 500° C. in a fixed-bed reactor and then used for a catalytic reaction. The reduced hybrid catalyst is used in a fixed-bed reactor under reaction conditions similar to those of a general methanol synthesis reaction, and specifically, the reaction temperature may be about 200° C. to about 400° C., the reaction pressure may be about 30 kg/cm' to about 60 kg/cm', and the space velocity may be about 1000 $h^{-1}$ to about 10000 $h^{-1}$. The hybrid catalyst prepared in this way has the advantage of producing a high yield from synthetic gas to dimethyl ether and less than about 1% of by-products in the total product, and additionally, the once conversion rate may be significantly increased to increase the efficiency of the reactor.

In the method for preparing methyl acetate, the synthetic gas may include hydrogen ($H_2$) and carbon monoxide (CO) in a mole ratio of about 1:2.5 to about 1:7.5, and may include about 8 mol % to about 30 mol % of carbon monoxide based on the total amount of the synthetic gas. If the mole ratio of carbon monoxide in the synthetic gas is less than about 2.5, the final methyl acetate production may be reduced, and if the mole ratio is greater than about 7.5, the deactivation of the entire catalytic system may be accelerated. In addition, when the synthetic gas includes less than 8 mol % of carbon monoxide, the final methyl acetate production may be reduced, and when it includes more than 30 mol %, the deactivation of the entire catalytic system may be accelerated.

Hereinafter, specific embodiments of the disclosure are presented. However, the examples described below are only for specifically illustrating or explaining the disclosure, and the scope of the disclosure is not limited thereto.

Experimental Example 1: Synthesis of Hybrid CZA/FER Catalyst

1) Synthesis of Nanosheet Ferrierite
1-1) Preparation of Precursor Mixed Solution After preparing a basic aqueous solution including a basic material, a silica source was added thereto and then, stirred for 1 hour, and a structural derivative material and an organic template material in a predetermined amount were added thereto. After adding the structural derivative material and the organic template material, the stirring was continued for 11 hours, and an alumina source was added thereto and further stirred for 12 hours, preparing a synthesis solution.

1-2) Hydrothermal Synthesis

The stirred synthesis solution was subjected to hydrothermal synthesis at 140° C. for 7 days by using a TEFLON (tetrafluoroethylene) reactor, and herein, the TEFLON (tetrafluoroethylene) reactor was stirred at 40 rpm to 60 rpm during the hydrothermal synthesis. After the 7 days' synthesis, ferrierite synthetic gel produced therefrom was washed with water and dried at 80° C. After the drying, the product was calcined at 450° C. to 650° C. for 6 hours to remove residual organic materials, synthesizing Na-form NS-NaFER(x)-pip-y and NS-NaFER(x)-pyrr-y.

Herein, x is a mole ratio of the organic template material/structural derivative material, pip and pyrr are respectively piperidine and pyrrolidine used as the structural derivative material, and y is the calcining temperature in the 1-2) and the 1-3).

1-3) Ion-Exchange

The synthesized NS-NaFER(x)-pip-y and NS-NaFER(x)-pyrr-y were subjected to ion exchange in a 1 M ammonium nitrate aqueous solution under stirring at 80° C. Through this process, Na-form ferrierite was converted into $NH_4$-form. The ion-exchanged ferrierite was calcined at 450° C. to 650° C. for 3 hours to remove $NH_4$, finally obtaining H-form nanosheet ferrierite of NS-HFER(x)-pip-y and NS-HFER(x)-pyrr-y.

The synthesized catalyst was compared with commercial ferrierite with respect to catalytic activity and physical properties, and the commercial ferrierite is named CFER.

2) Co-Precipitation

The synthesized nanosheet ferrierite zeolite and the commercial ferrierite were used to co-precipitate Cu/ZnO/$Al_2O_3$, for which a first solution, a second solution, and a third solution were respectively prepared.

The prepared nanosheet ferrierite zeolite and the commercial ferrierite were dissolved respectively by 1 g in 200 ml of distilled water, preparing the first solution including a ferrierite support.

The second solution was prepared by completely dissolving copper nitrate, zinc nitrate, and aluminum nitrate in 200 ml of distilled water to have a mole ratio of Cu:Zn:Al=7:3:1.

The third solution of a basic precipitating agent with pH 7 or higher was prepared by completely dissolving 7 g of carbonate ammonium in 200 ml of distilled water.

The second solution and the third solution were simultaneously added dropwise to the first solution at an each appropriate rate, while the first solution was maintained at 70° C. with pH 7. After dropping all the second solution into the first solution, aging was performed by maintaining 70° C. and pH 7 for 1 hour. After the aging, precipitates formed therein were washed and dried and then, calcined at 350° C. for 3 hours, completing a hybrid CZA/FER catalyst synthesis.

Depending on a FER support used therein, the obtained catalysts were called to be CZA/NS0.1, CZA/NS0.3, and CZA/CFER. Herein, CZA/NS0.1 is the NS-HFER 0.1-pip-550, and CZA/NS0.3 is NS-HFER 0.3-pip-550.

Example 1

A catalyst was prepared according to the same method as Experimental Example 1 and named as CZA/NS0.1.

Example 2

A catalyst was prepared according to the same method as Experimental Example 1 and named as CZA/NS0.3.

Example 3

A catalyst was prepared according to the same method as Experimental Example 1 and named as NS-HFER(0.08)-pip-550.

Example 4

A catalyst was prepared according to the same method as Experimental Example 1 and named as NS-HFER(0.1)-pip-550.

Example 5

A catalyst was prepared according to the same method as Experimental Example 1 and named as NS-HFER(0.3)-pip-550.

Example 6

A catalyst was prepared according to the same method as Experimental Example 1 and named as NS-HFER(0.1)-pyrr-550.

Comparative Example 1

A catalyst was prepared according to the same method as Experimental Example 1 and named as CZA/CFER.

Comparative Example 2

A catalyst was prepared according to the same method as Experimental Example 1 and named as NS-HFER(0.01)-pip-550.

Comparative Example 3

A catalyst was prepared according to the same method as Experimental Example 1 and named as NS-HFER(0.5)-pip-550.

Comparative Example 4

A catalyst was prepared according to the same method as Experimental Example 1 and named as NS-HFER(0.1)-pip-450.

Comparative Example 5

A catalyst was prepared according to the same method as Experimental Example 1 and named as NS-HFER(0.1)-pip-650.

Comparative Example 6

CFER was used as commercial FER.

Experimental Example 2: Reaction Experiment

1) Conversion Reaction from Synthetic Gas into Dimethyl Ether

The conversion reaction from the synthetic gas into dimethyl ether by using the synthesized hybrid CZA/FER catalyst proceeded as follows.

Before the reaction, 0.4 g of catalyst was loaded in a ⅜ inch reactor and reduced by using $H_2$/Ar mixed gas. After the reduction, a reactivity experiment was performed under the following conditions to check if reactivity changed depending on a temperature, and then, a long term reaction was performed at an optimal temperature. In other words, a mixed gas of $CO/CO_2/N_2/H_2$=21/9/4/66 and $CO/CO_2/N_2/H_2/CH_4$=8/8/2/60/22 was used under 50 bars at space velocity of 5000 $L/kg_{cat}$/to perform the reaction at 220° C., 250° C., 270° C., and 290° C. respectively for 10 hours, that is, for 40 hours in total and then, at the fixed temperature of 270° C. for 40 hours. After the reaction, a product therefrom was analyzed by using gas chromatography to mainly obtain a CO conversion rate, MeOH/DME selectivity, and DME production.

2) Conversion Reaction from Dimethyl Ether into Methyl Acetate

A conversion reaction of the synthesized hybrid CZA/FER catalyst from dimethylether to methylacetate was performed as follows.

First, the catalyst was pre-treated with nitrogen at 500° C. for 1 hour to remove water and foreign materials adsorbed thereon. After the pre-treatment, the reaction experiment was performed by using a mixed gas of dimethylether/carbon monoxide/nitrogen. In other words, the reaction experiment was performed at 220° C. under 10 bars at 2000 $L/kg_{cat}$/h by using each mixed gas of $DME/CO/N_2$=5/45/50, 4.5/90/5.5, and 1/50/49, wherein each mixed gad had a mole ratio of dimethylether/carbon monoxide=1/9, 1/20, and 1/50. An amount of the catalyst used in the reaction was 0.4 g, and the reaction was performed by using a ⅜-inch fixed-bed reactor. A product produced during the reaction was analyzed through gas chromatography. As for the dimethylether conversion rate, a maximum value was recorded, and the carbon selectivity was obtained by measuring an average during a steady state (for about 5 hours to about 10 hours before completing the reaction). The deactivation rate was defined by an average variation rate from the highest conversion point to the last reaction point.

3) Conversion Reaction from Synthetic Gas Via Dimethyl Ether (Dual-Bed Condition) into Methyl Acetate A methylacetate conversion reaction of the synthesized hybrid CZA/FER catalyst from the synthetic gas via dimethylether proceeded as follows.

A selected hybrid CZA/FER catalyst and nanosheet ferrierite as a dual-bed were put in a fixed-bed reactor, and while synthetic gas ($CO/CO_2/N_2/H_2$=21/9/4/66) was continuously injected thereinto, methylacetate was synthesized in one-step by maintaining 50 bars, space velocity of 5000 $L/kg_{cat}$/h, and a reaction temperature of 220° C., 250° C., 280° C., and 300° C. each by 10 hours for 40 hours in total. After the reaction, the gas was analyzed by using gas chromatography to calculate a CO conversion rate, MeOH/DME/MA selectivity, and MA productivity.

The dimethylether synthesis reaction results from the synthetic gas are shown in Tables 1 to 3.

The methylacetate synthesis reaction results from the dimethylether are shown in Table 4.

In addition, the catalysts according to Example 6 and Comparative Example 6 were used with each mixed gas having a different composition of $DME/CO/N_2$=4.5/90/5.5 and 1/50/49 to perform dimethylether carbonylation, and the results are shown in Table 5.

When the catalysts according to Examples 1 and 4 as a dual-bed were loaded to perform a conversion reaction of synthetic gas, MA was successfully synthesized. Herein, in the upper bed, the CZA/NS0.1 catalyst of Example 1 was loaded, and in the lower bed, the NS-HFER(0.1)-pip-550 catalyst of Example 4 was loaded. Under the constant conditions of space velocity of 5000 L/kgcat/h and pressure of 50 bars, the temperature was changed into 220° C., 250° C., 280° C., and 300° C. to check reactivity, and the results are shown in Table 6.

TABLE 1

| Gas composition/ temperature $[CO/CO_2/H_2]$/ [° C.] | Catalyst | CO conversion rate max. [%] | DME selectivity max. [%] | Deactivation rate [%/h · $(m^2/Cu)$] | DME productivity $[g_{DME}/kg_{cat} · h]$ |
|---|---|---|---|---|---|
| 21/9/66/270 | Example 1/ CZA/NS0.1 | 69.1 | 97.0 | 0.012 | 1145.4 |
|  | Example 2/ CZA/NS0.3 | 65.5 | 95.3 | 0.017 | 1048.1 |

TABLE 1-continued

| Gas composition/ temperature [CO/CO$_2$/H$_2$]/ [° C.] | Catalyst | CO conversion rate max. [%] | DME selectivity max. [%] | Deactivation rate [%/h · (m$^2$/Cu)] | DME productivity [g$_{DME}$/kg$_{cat}$ · h] |
|---|---|---|---|---|---|
| | Comparative Example 1/ CZA/CFER | 25.5 | 92.7 | 0.021 | 410.3 |

TABLE 2

| Gas composition [CO/CO$_2$/H$_2$] | Catalyst | Temperature | CO conversion rate max. [%] | DME selectivity max. [%] | DME productivity [g$_{DME}$/kg$_{cat}$ · h] |
|---|---|---|---|---|---|
| 21/9/66 | Example 1/ CZA/NS0.1 | 220 | 7.0 | 71.3 | 199.7 |
| | | 250 | 39.9 | 86.8 | 713.7 |
| | | 270 | 65.7 | 90.2 | 1139.1 |
| | | 290 | 72.4 | 90.0 | 1262.6 |
| | Example 2/ CZA/NS0.3 | 220 | 16.7 | 56.9 | 266.8 |
| | | 250 | 52.1 | 80.2 | 809.0 |
| | | 270 | 66.3 | 84.9 | 1048.8 |
| | | 290 | 68.3 | 86.2 | 1090.7 |
| | Comparative Example 1/ CZA/CFER | 220 | 2.2 | 70.8 | 61.3 |
| | | 250 | 10.5 | 80.5 | 191.6 |
| | | 270 | 22.5 | 84.6 | 370.7 |
| | | 290 | 39.9 | 87.5 | 638.2 |

TABLE 3

| Gas composition [CO/CO$_2$/H$_2$] | Catalyst | Temperature | CO conversion rate max. [%] | DME selectivity max. [%] | DME productivity [g$_{DME}$/kg$_{cat}$ · h] |
|---|---|---|---|---|---|
| 8/8/60 | Example 1/ CZA/NS0.1 | 220 | 21.5 | 70.6 | 174.9 |
| | | 250 | 62.0 | 84.7 | 450.7 |
| | | 270 | 72.8 | 82.1 | 546.8 |
| | | 290 | 68.7 | 83.3 | 531.5 |

Referring to Tables 1 to 3, the catalysts of the examples co-precipitated on the nanosheet ferrierite exhibited excellent catalytic activity and high DME productivity regardless of reaction conditions.

TABLE 4

| Gas composition [DME:CO:N$_2$] (mol %) | Catalyst | Conversion rate [DME] (mol %) | Carbon selectivity [MA/MeOH] (mol %) | Deactivation rate (mol %/h) |
|---|---|---|---|---|
| 5/45/50 | Example 3/NS-HFER 0.08-pip-550 | 13.6 | 96.5/3.5 | 0.05 |
| | Example 4/NS-HFER 0.1-pip-550 | 25.9 | 97.6/2.4 | 0.09 |
| | Example 5/NS-HFER 0.3-pip-550 | 24.4 | 95.9/4.1 | 0.12 |
| | Comparative Example 2/NS-HFER 0.01-pip-550 | 17.6 | 93.8/6.2 | 0.04 |
| | Comparative Example 3/NS-HFER 0.5-pip-550 | 4.2 | 91.6/8.4 | — |
| | Comparative Example 4/NS-HFER 0.1-pip-450 | 16.9 | 94.8/5.2 | 0.08 |
| | Comparative Example 5/NS-HFER 0.1-pip-650 | 5.0 | 92.5/7.5 | — |
| | Comparative Example 6/CFER | 15.8 | 89.4/10.6 | 0.1 |

TABLE 5

| Gas composition [DME:CO:N$_2$] (mol %) | Catalyst | Conversion rate [DME] (mol %) | Carbon selectivity [MA/MeOH] (mol %) | Deactivation rate (mol %/h) |
|---|---|---|---|---|
| 5.5/90/4.5 | Example 6/NS-HFER 0.1-pyrr-550 | 40.1 | 98.6/0.8 | 0.11 |
| 1/50/49 | Example 6/NS-HFER 0.1-pyrr-550 | 37.9 | 98.5/1.5 | 0.05 |
| 5.5/90/4.5 | Comparative Example6/CFER | 16.9 | 98.6/1.2 | 0.13 |
| 1/50/49 | Comparative Example6/CFER | 17.9 | 100/0 | 0.07 |

TABLE 6

| Catalyst [1$^{st}$ bed/2$^{nd}$ bed] (g/g) | Temperature (° C.) | CO conversion rate (%) | Selectivity [DME/MA] (%) | Productivity [DME/MA] (kg/kg · h) |
|---|---|---|---|---|
| Example 1/ Example 4 (0.2/0.4) | 220 | 20.1 | 91.2/0.8 | 437.9/5.9 |
| | 250 | 48.6 | 90.0/2.5 | 852.4/38.1 |
| | 270 | 55.3 | 78.2/8.0 | 830.3/134.7 |
| | 300 | 50.0 | 52.3/10.7 | 568.1/186.2 |
| Example 1/ Example 4 (0.4/0.4) | 220 | 49.2 | 90.9/0.2 | 858.2/2.5 |
| | 250 | 64.8 | 90.0/1.1 | 1066.8/20.1 |
| | 270 | 60.4 | 83.1/4.0 | 951.6/72.3 |
| | 300 | 47.0 | 66.5/7.7 | 642.0/119.7 |

Referring to Tables 4 to 6, the prepared nanosheet ferrierite catalysts exhibited increased activity and stability according to the gas compositions, compared with commercial CFER of Comparative Example 6.

Experimental Example 3: Hybrid CZA/FER Physical/Structural Analysis

Figure 3:
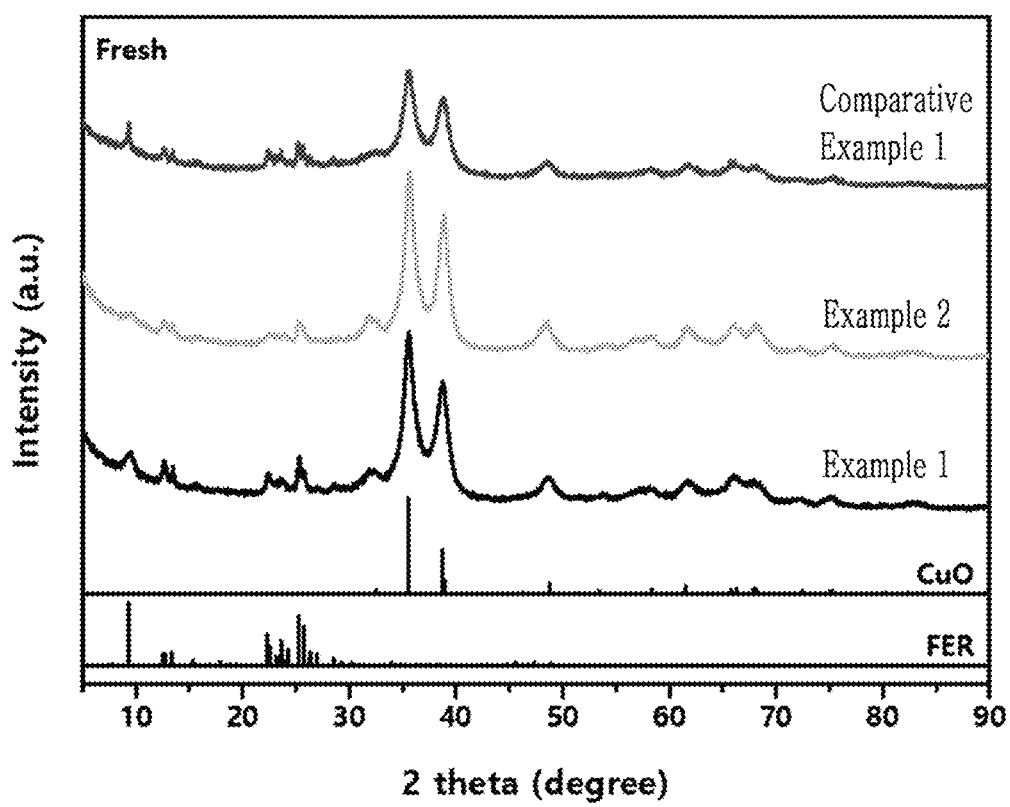
FIG. 3 is a graph showing the XRD measurement results of the hybrid CZA/FER catalyst in Experimental Example 3.
Figure 4:
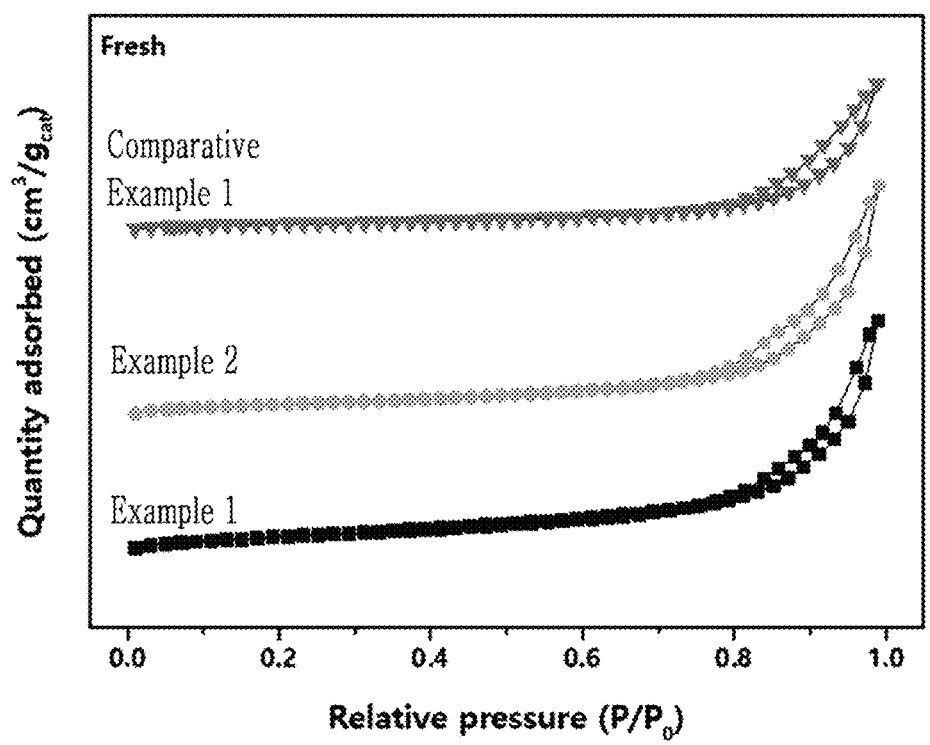
FIG. 4 is a graph showing the $N_2$-sorption measurement result of the hybrid CZA/FER catalyst in Experimental Example 3.
Figure 5:
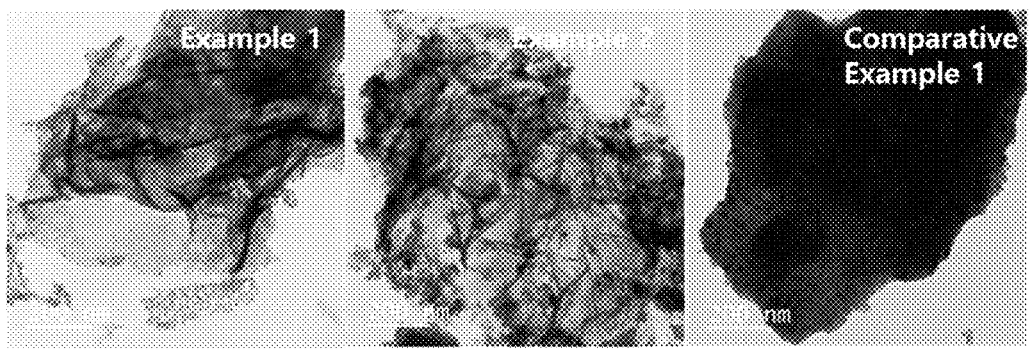
FIG. 5 is a photograph showing the TEM measurement result of the hybrid CZA/FER catalyst in Experimental Example 3.

Physical/structural characteristics of the prepared hybrid CZA/FER catalysts were examined by performing XRD, N$_2$-sorption, and TEM, and the results are shown in FIGS. 3 to 5.

In addition, the N$_2$-sorption was used to measure a BET specific surface area, and the results are shown in Table 7.

TABLE 7

| | N$_2$-sorption [specific surface area/outer surface area/micropore volume] (m$^2$/g$_{cat}$/m$^2$/g$_{cat}$/cm$^3$/g$_{cat}$) | $^{29}$Si NMR [Si (0Al)] (%) |
|---|---|---|
| Example 3 | 446.44/166.31/0.129 | 69.28 |
| Example 4 | 451.73/198.09/0.117 | 73.79 |

TABLE 7-continued

| | N$_2$-sorption [specific surface area/outer surface area/micropore volume] (m$^2$/g$_{cat}$/m$^2$/g$_{cat}$/cm$^3$/g$_{cat}$) | $^{29}$Si NMR [Si (0Al)] (%) |
|---|---|---|
| Example 5 | 504.58/265.14/0.109 | 71.81 |
| Comparative Example 2 | 389.26/84.94/0.141 | 67.95 |
| Comparative Example 3 | 462.19/255.68/0.094 | 60.03 |
| Comparative Example 4 | 380.47/129.24/0.116 | 77.21 |

TABLE 7-continued

| | N$_2$-sorption [specific surface area/outer surface area/micropore volume] (m$^2$/g$_{cat}$/m$^2$/g$_{cat}$/cm$^3$/g$_{cat}$) | $^{29}$Si NMR [Si (0Al)] (%) |
|---|---|---|
| Comparative Example 5 | 458.62/198.59/0.120 | 69.07 |
| Comparative Example 6 | 371.59/46.81/0.124 | 70.42 |

The XRD analysis simultaneously confirmed an XRD diffraction pattern unique to ferrierite and a diffraction pattern of Cu, and the BET specific surface area results confirmed an area changing according to characteristics of a support ferrierite. In addition, the TEM images clearly visually exhibited structures of the support ferrierites affecting specific surface area changes.

The prepared nanosheet ferrierite catalysts, unlike commercial ferrierite, exhibited a thin structure, which improved mass transfer ability and thus increased reactivity and stability. The mass transfer ability and the large specific surface area due to the thin structure, despite low crystallinity of the nanosheet ferrierite, improved catalytic activity in the conversion reaction of dim ethyl ether.

Experimental Example 4: Analysis of Hybrid CZA/FER Chemical Characterization

Figure 6:
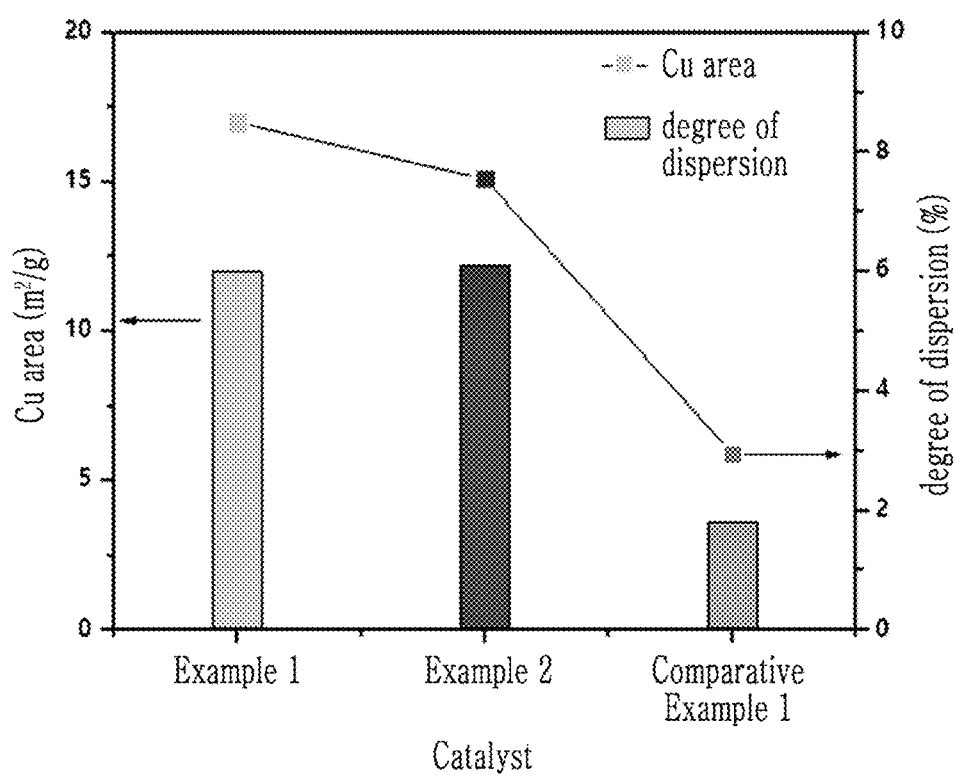
FIG. 6 is a graph showing the measurement result of $N_2O$-chemisorption of the hybrid CZA/FER catalyst in Experimental Example 4.
Figure 7A:
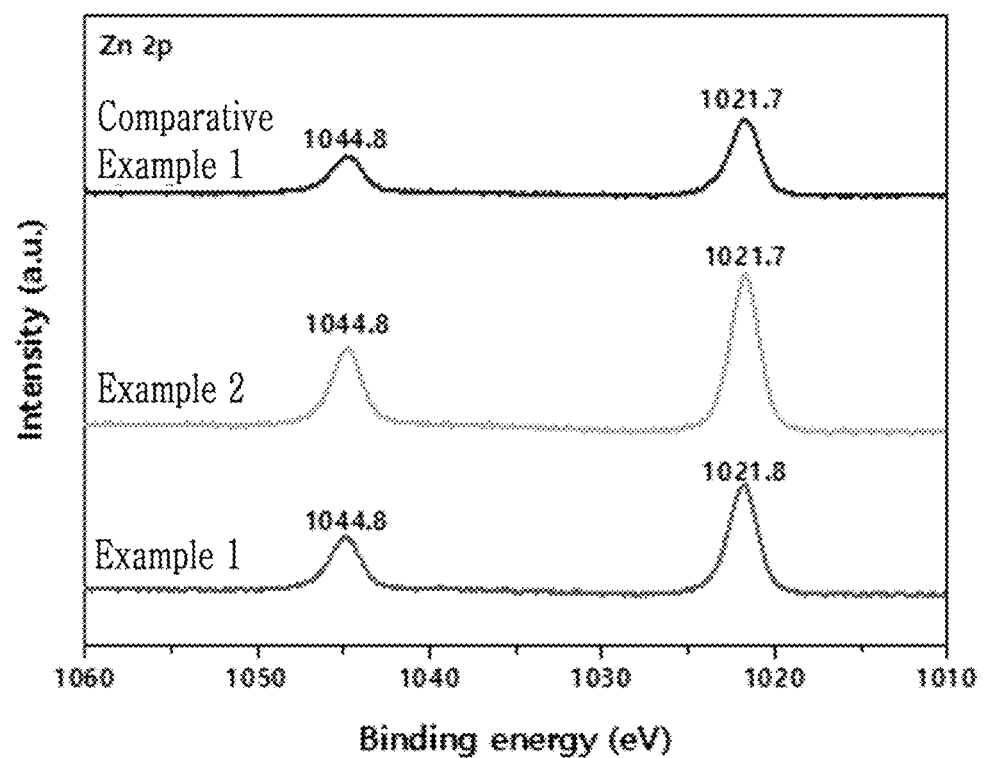
FIGS. 7A, 7B, and 7C are graphs showing the XPS measurement results of the hybrid CZA/FER catalyst in Experimental Example 4.
Figure 7B:
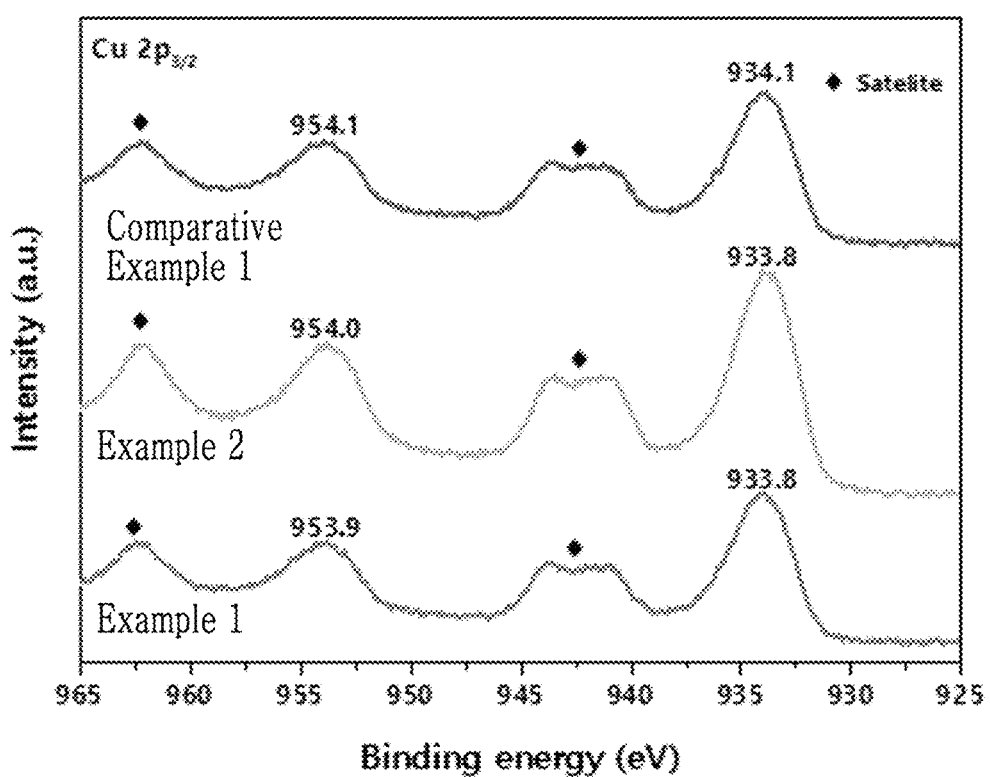
Figure 7C:
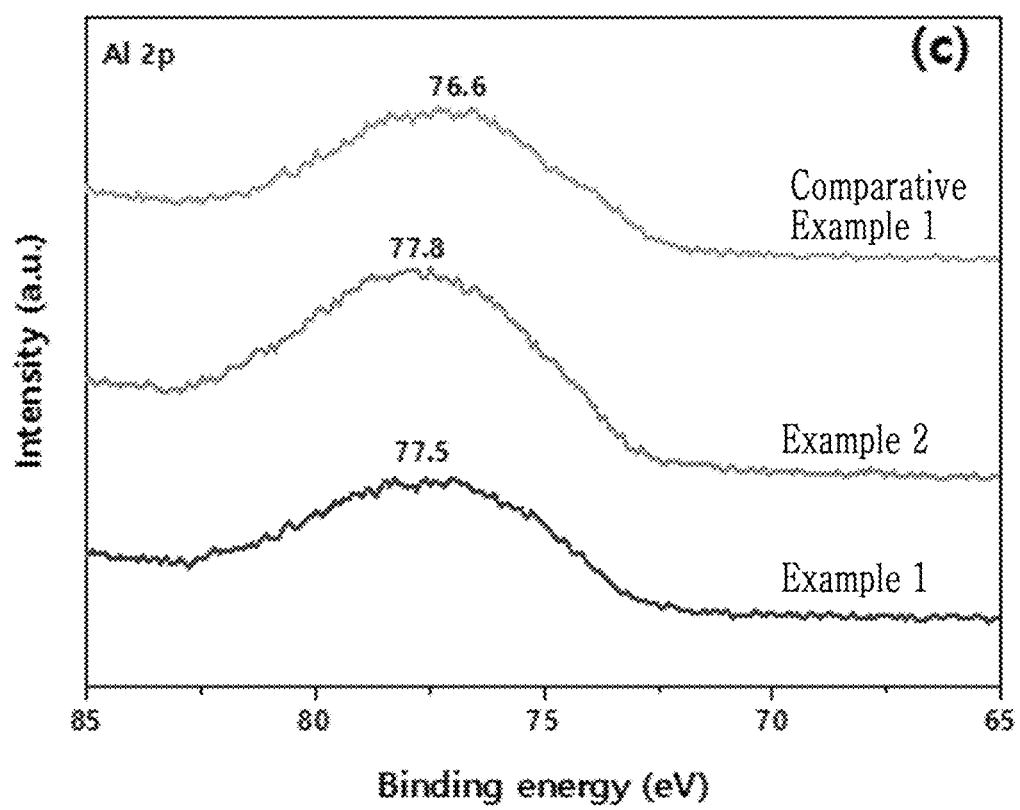

Chemical characteristics of the prepared hybrid CZA/FER catalyst were analyzed by performing N$_2$O-chemisorption, XPS, NH$_3$-TPD, and H$_2$-TPR, and the results are respectively shown in FIGS. 6 and 7 and Table 8.

Specifically, after performing the N$_2$O-chemisorption analysis, N$_2$O and Cu chemical adsorption patterns were examined to quantitatively obtain an area and a degree of dispersion of Cu present on CZA/FER. After performing the XPS analysis, relative ratios of Cu, Zn, and Al metals in the CZA/FER catalyst were calculated. The NH$_3$-TPD analysis was performed by making NH$_3$ sufficiently adsorb to acid sites in CZA/FER at 100° C. and then, increasing the temperature up to 450° C. to measure an amount of NH$_3$. Through the analysis, a TPD pattern of each CZA/FER catalyst was obtained to measure an area, and the area was used to quantitatively obtain acid sites in each catalyst. In addition, the H$_2$-TPR analysis was performed to examine reducibility of CZA/FER and stability of Cu species by using H$_2$. Herein, a TPR spectrum was obtained by increasing a temperature up to 400° C., while H$_2$/Ar (=5/95) gas was continuously flowed, and then, O$_2$/He (=1/99) gas was used to sufficiently perform oxidation, and reduction was performed again under the same condition. After the analysis, two consecutive reduction temperatures were checked to examine how easily Cu species in each support FER were reduced, and whether or not the reducibility was maintained after the oxidation.

TABLE 8

| Catalyst | N$_2$-sorption [specific surface area/ pore volume/pore size] (m$^2$/g/cm$^3$/g nm) | XPS [Cu/Al ratio/ Cu/Zn ratio] (a.u/a.u.) | N$_2$O-chemi- sorption [Cu area/ dispersion degree] (m$^2$/g/%) | NH$_3$-TPD [acid site] (mmol/g) | H$_2$-TPR [1$^{st}$ reduction temperature/ 2$^{nd}$ reduction temperature] (° C./° C.) |
|---|---|---|---|---|---|
| Example 1/ CZA/NS0.1 | 129.5/0.413/12.8 | 2.67/0.79 | 17.0/6.0 | 0.647 | 185-222/215 |
| Example 2/ CZA/NS0.3 | 113.0/0.411/14.5 | 2.68/0.79 | 15.1/6.1 | 0.736 | 213/222 |
| Comparative Example 1/ CZA/CFER | 82.3/0.269/13.1 | 2.60/1.07 | 5.9/1.8 | 0.555 | 214/230 |

Referring to Table 8, even though the same amounts of metal precursors were co-precipitated in the same method, the catalysts exhibited overall characteristic changes depending on a support ferrierite of the nanosheet ferrierite and the commercial ferrierite.

The most obvious difference was found in a distribution of Cu, which is reaction sites, that is, a higher degree of Cu dispersion due to a large specific surface area and a unique structure and thus a larger Cu surface area per unit catalyst weight in the nanosheet ferrierite with a thin structure than in the commercial ferrierite support. After the support, the specific surface area of the entire catalyst itself was large, and after the XPS analysis, a relatively large amount of Cu species was found.

In H$_2$-TPR, Cu present in the nanosheet ferrierite was easily reduced, and since a reduction temperature did not increase in a first reduction and even a second reduction after oxidation, the Cu species were more sufficiently reduced.

In addition, the amount of acid sites in a ferrierite support where DME conversion of synthetic gas finally occurred, after Cu/ZnO/Al$_2$O$_3$ co-precipitation, was larger, in the nanosheet ferrierites of CZA/NS0.1 (Example 1) and CZA/NS0.3 (Example 2) than in the commercial ferrierite (Comparative Example 1). Accordingly, Cu/ZnO/Al$_2$O$_3$ was precipitated on the nanosheet ferrierite support to develop excellent hybrid CZA/FER and optimize reaction sites, resultantly confirming high DME productivity.

Experimental Example 5: Analysis of Nanosheet Ferrierite Structure

Figure 8:
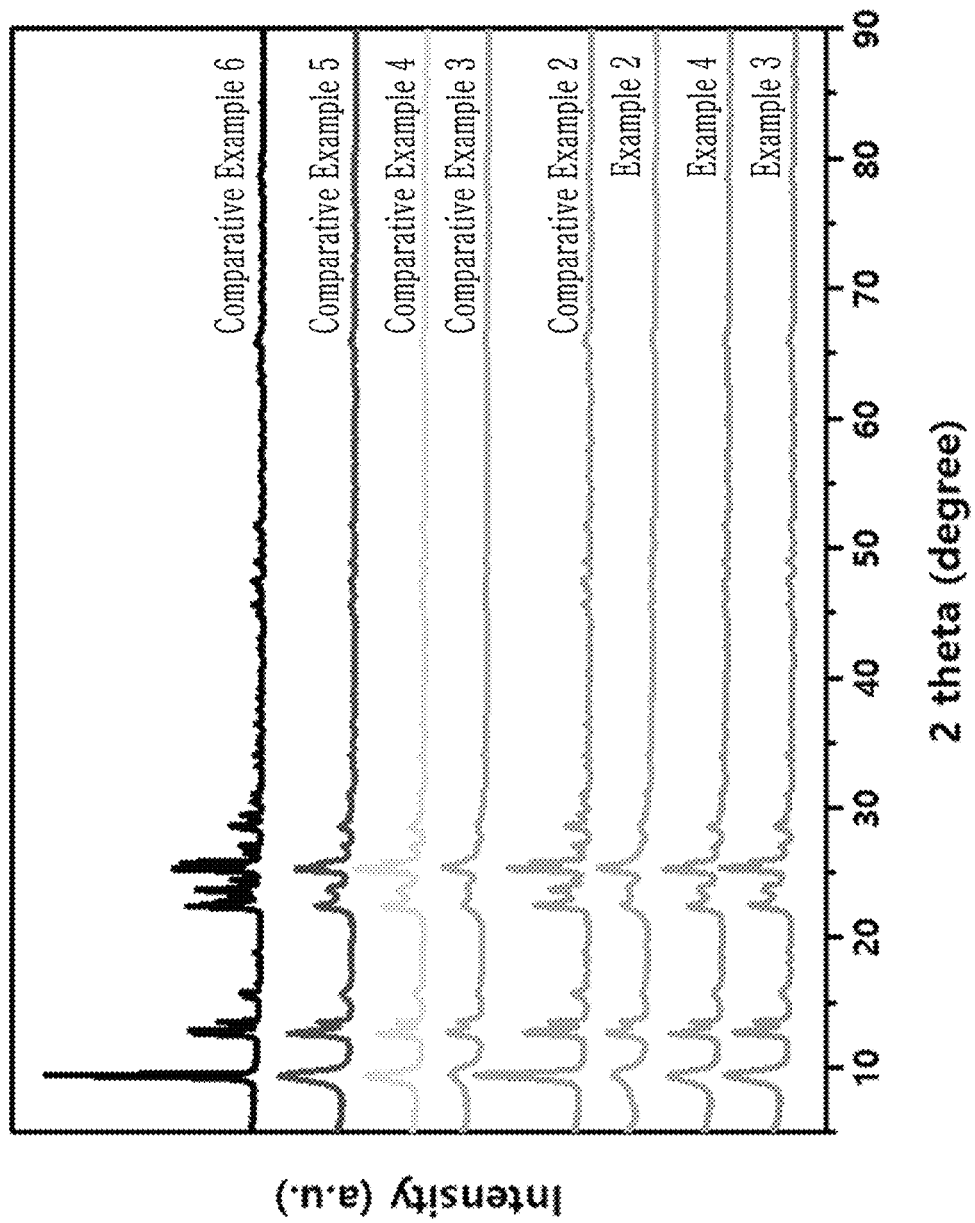
FIG. 8 is a graph showing the XRD measurement results of the nanosheet ferrierite in Experimental Example 5.

Crystal characteristics of the prepared nanosheet ferrierite were examined by performing an XRD analysis, and the XRD pattern is shown in FIG. 8.

Figure 9:
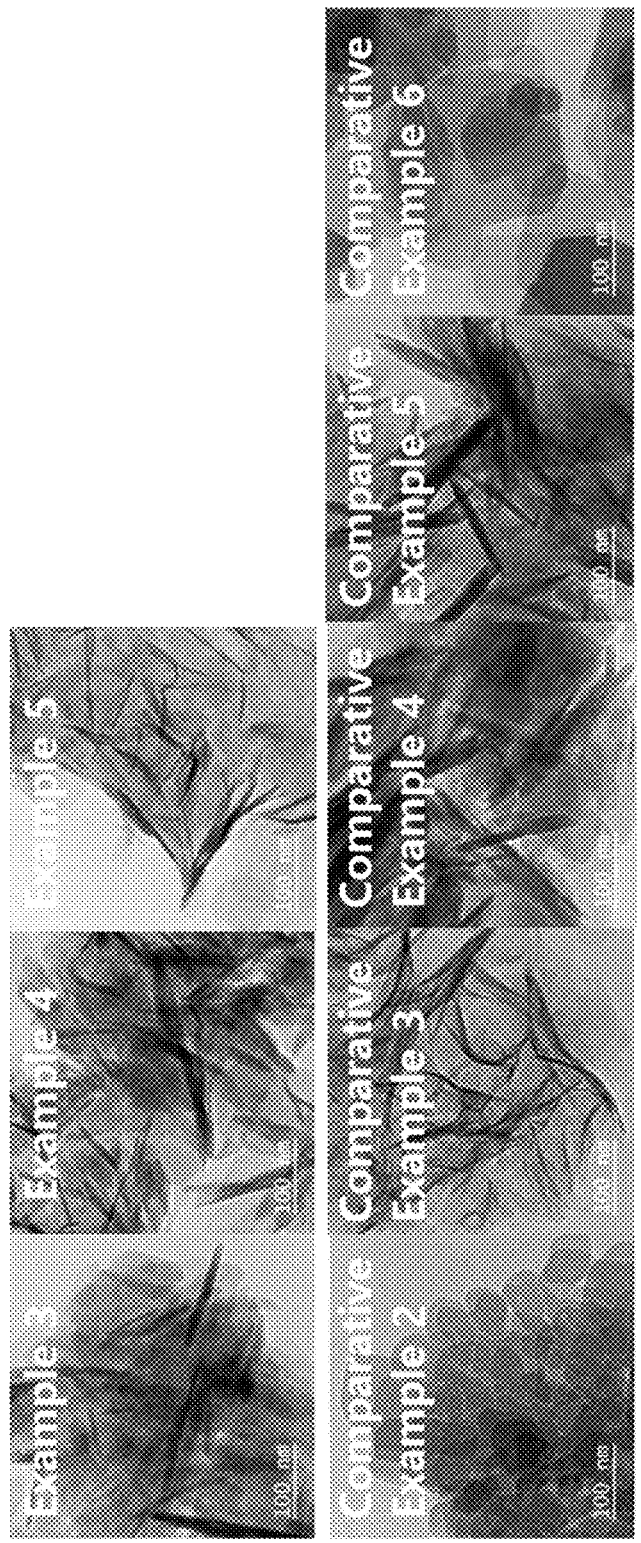
FIG. 9 is a graph showing the TEM measurement results of the nanosheet ferrierite according to Examples 3 to 5 and Comparative Examples 2 to 6.
Figure 10:
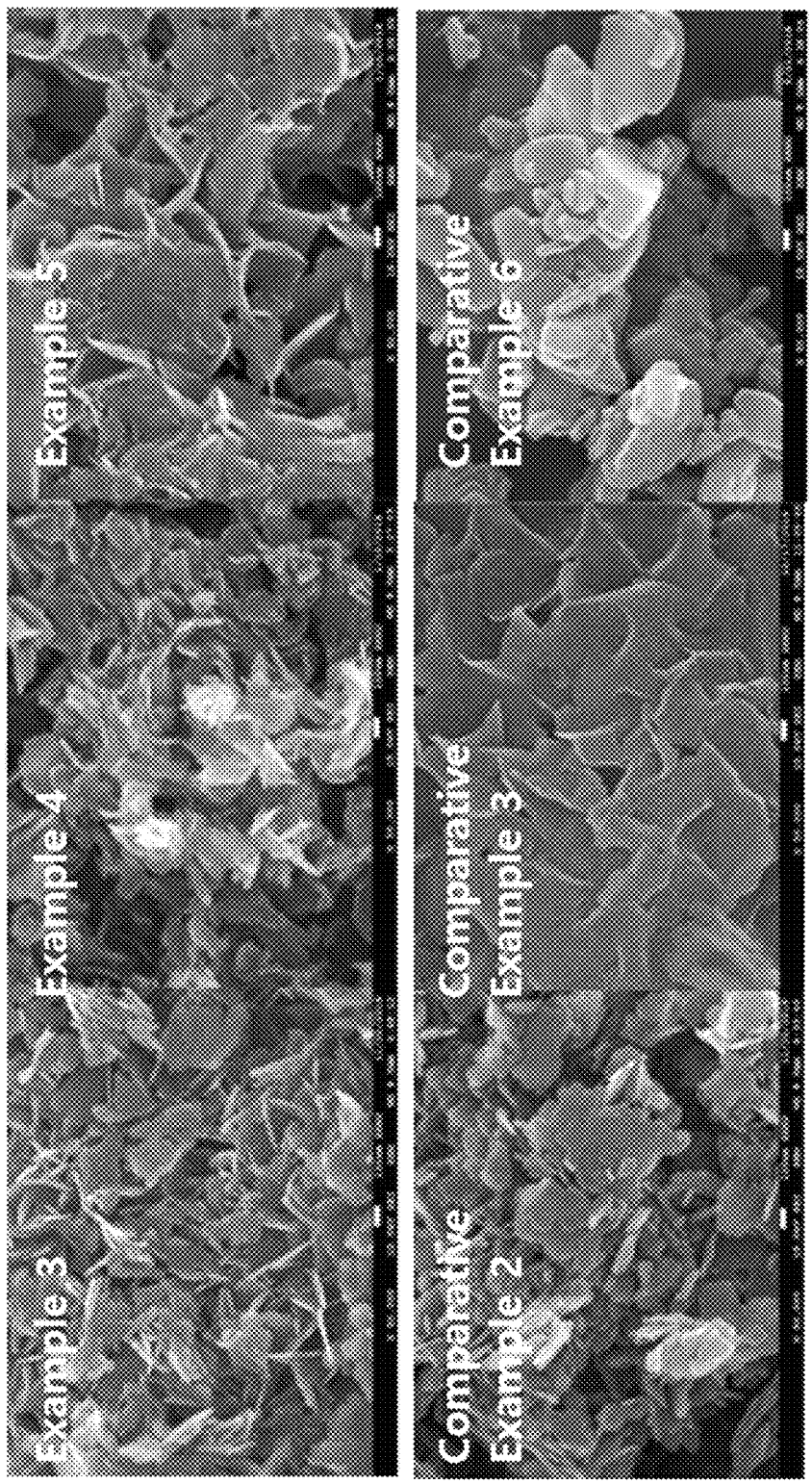
FIG. 10 is a graph showing the SEM measurement results of the nanosheet ferrierite according to Examples 3 to 5 and Comparative Examples 2, 3 and 6.

In addition, structural images of corresponding catalysts were examined by performing SEM and TEM analyses, and the results are shown in FIGS. 9 and 10.

The SEM and TEM analyses visually confirmed extremely thin structure unique to the nanosheet ferrierite and also, directly confirmed properties changed depending on a synthesis condition. In addition, crystallinity of the corresponding catalysts was confirmed through the XRD analysis and then, compared with an XRD pattern unique to a ferrierite, to judge whether or not a ferrierite was successfully synthesized in a nanosheet synthesis method. Furthermore, specific surface areas and silicon bonding characteristics were examined to check property changes of a catalyst according to synthesis conditions, succeeding in deriving structurally optimized synthesis conditions.

Experimental Example 6: Acid Site Analysis of Nanosheet Ferrierite

Ammonia TPD ($NH_3$-TPD) and pyridine IR(Py-IR) were performed to check acid sites of the prepared nanosheet ferrierite. After adsorbing basic materials such as ammonia and pyridine to the acid sites, an amount of the acid sites in the nanosheet ferrierite was quantitatively measured through each analysis. The analysis results are provided in Table 9.

The ammonia had a small molecular size and thus was adsorbed to all the acid sites in a zeolite framework. On the contrary, the pyridine had a large molecular size and was limitedly adsorbed only to ten member rings in ferrierite. In addition, due to the different characteristics of the analytical technique, Brönsted acid sites and Lewis acid sites were distinguished and quantified through IR. TPD was used to quantify the amount of weak acid, medium acid, and strong acid according to the strength of the acid sites. Accordingly, TPD and IR analysis results were combined to selectively quantify the Brönsted acid sites in 8 membered-rings, which are main reaction sites of a dimethylether carbonylation reaction. In addition, the Lewis acid sites in IR and the weak acid and medium acid in TPD are in general known as defect points of zeolite catalysts.

TABLE 9

| | $NH_3$-TPD [weak acid/ medium acid/ strong acid] (mmol/$g_{cat}$) | Py-IR [Brönsted/ Lewis] (mmol/ $g_{cat}$/×10$^2$ mmol/$g_{cat}$) | 8-MR acid site (mmol/ gcat) |
|---|---|---|---|
| Example 3 | 0.590/0.195/0.452 | 0.202/3.130 | 0.250 |
| Example 4 | 0.622/0.118/0.552 | 0.266/3.405 | 0.286 |
| Example 5 | 0.562/0.243/0.423 | 0.126/3.962 | 0.297 |
| Comparative Example 2 | 0.678/0.266/0.306 | 0.210/2.466 | 0.096 |
| Comparative Example 3 | 0.212/0.444/— | 0.032/1.994 | — |
| Comparative Example 4 | 0.798/0.129/0.379 | 0.060/0.556 | 0.319 |
| Comparative Example 5 | 0.515/0.611/0.046 | 0.096/3.397 | — |
| Comparative Example 6 | 0.961/0.104/0.537 | 0.140/0.634 | 0.397 |

Referring to Table 9, the nanosheet ferrierite exhibited optimized acid sites in addition to structural specificity and superiority. Particularly, the amount of the Brönsted acid sites in 8-MR in which a conversion of dimethylether to methylacetate selectively occurred was the largest in the most optimized catalysts of Examples 4 and 5. Accordingly, the 8-MR Brönsted acid sites increased after the nanosheet synthesis contributed to a higher dimethylether conversion rate than a general commercial catalyst.

Experimental Example 7: Coke Analysis of Nanosheet Ferrierite

After the catalytic reaction, coke deposited in the synthesized nanosheet ferrierite was analyzed to examine how the coke deposition affected catalyst characteristics and deactivation by performing TGA and $H_2$-TPSR. TGA and $H_2$-TPSR results are provided in Table 10.

In TGA, a deposition amount of the coke was relatively obtained by measuring a decreased mass after removing the coke by increasing a temperature up to 1000° C., while air was flowed into a catalyst after a reaction of depositing the coke and increasing the weight. In $H_2$-TPSR, a type of the deposited coke was identified by increasing the temperature up to 1000° C., while $H_2$ gas was flowed into the catalyst after the reaction to examine how the coke reacted with $H_2$ at each temperature.

As a result of $H_2$-TPSR, three characteristic peaks were identified, and the deposited coke was broadly classified into three types. In addition, the coke showing a peak at the highest temperature was the heaviest and had a largest molecular weight among the deposited coke types. Accordingly, how synthesis conditions affected the coke deposition and deactivation during the catalytic reaction was understood.

TABLE 10

| | $H_2$-TPSR [α peak/β peak γ peak] (%) | TG (%) |
|---|---|---|
| Example 4 | 6.03/7.34/11.81 | 89.69 |
| Example 5 | 3.35/3.61/4.46 | 89.78 |
| Example 6 | 0.8/8.09/7.46 | 89.35 |
| Comparative Example 2 | 7.27/1.75/5.76 | 90.17 |
| Comparative Example 3 | 4.52/8.46/7.31 | 92.36 |
| Comparative Example 4 | 3.05/8.65/27.9 | 85.94 |
| Comparative Example 5 | 0.72/11.35/7.05 | 91.26 |
| Comparative Example 6 | 11.22/4.41/33.56 | 83.70 |

Referring to Table 10, the coke deposition involved in the deactivation of catalysts was also greatly reduced in the nanosheet ferrierite.

While this disclosure has been described in connection with what is presently considered to be practical example embodiments, it is to be understood that the disclosure is not limited to the disclosed embodiments. On the contrary, it is intended to cover various modifications and equivalent arrangements included within the spirit and scope of the appended claims.

The invention claimed is:

1. A hybrid CZA/FER catalyst comprising:
   a nanosheet ferrierite zeolite; and
   a Cu—Zn—Al-based oxide supported on the nanosheet ferrierite zeolite;
   wherein the nanosheet ferrierite zeolite has a shape in which one or more sheets having a thickness of about 5 nm to about 10 nm and a width of about 100 nm to about 150 nm are stacked; and
   wherein an amount of weak acid sites in the nanosheet ferrierite measured through NH3-TPD analysis is about 0.562 mmol/$g_{cat}$ to about 0.736 mmol/$g_{cat}$;
   an amount of medium acid sites in the nanosheet ferrierite measured through NH3-TPD analysis is about 0.118 mmol/$g_{cat}$ to about 0.243 mmol/$g_{cat}$;
   an amount of strong acid sites in the nanosheet ferrierite measured through NH3-TPD analysis is about 0.423 mmol/$g_{cat}$ to about 0.552 mmol/$g_{cat}$;
   an amount of Brönsted acid sites in the nanosheet ferrierite measured through Py-IR analysis is about 0.126 mmol/$g_{cat}$ to about 0.266 mmol/$g_{cat}$;
   an amount of Lewis acid sites in the nanosheet ferrierite measured through Py-IR analysis is about 3.130×102 mmol/$g_{cat}$ to about 3.962×102 mmol/$g_{cat}$; or an amount of Brönsted acid sites in 8 membered-rings of the nanosheet ferrierite combined NH3-TPD and Py-IR analysis results is about 0.250 mmol/$g_{cat}$ to about 0.297 mmol/$g_{cat}$.

2. The hybrid CZA/FER catalyst of claim 1, wherein the Cu—Zn—Al-based oxide comprises about 40 wt % to about 60 wt % of CuO, about 35 wt % to about 45 wt % of ZnO, and about 5 wt % to about 15 wt % of $Al_2O_3$ based on the total weight of the Cu—Zn—Al-based oxide.

3. The hybrid CZA/FER catalyst of claim 1, wherein the hybrid CZA/FER catalyst comprises about 0.1 part by weight to about 5 parts by weight of the Cu—Zn—Al-based oxide based on 1 part by weight of the nanosheet ferrierite zeolite.

* * * * *